(12) United States Patent
Fukuda et al.

(10) Patent No.: US 9,192,321 B2
(45) Date of Patent: Nov. 24, 2015

(54) APPARATUS FOR MEASURING BODY FAT

(75) Inventors: Hiroaki Fukuda, Gurgaon (IN); Tatsuya Takahashi, Osaka (JP); Yoshie Terazono, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 517 days.

(21) Appl. No.: 13/581,586

(22) PCT Filed: Mar. 24, 2011

(86) PCT No.: PCT/JP2011/057090
§ 371 (c)(1),
(2), (4) Date: Aug. 28, 2012

(87) PCT Pub. No.: WO2011/118678
PCT Pub. Date: Sep. 29, 2011

(65) Prior Publication Data
US 2012/0330124 A1 Dec. 27, 2012

(30) Foreign Application Priority Data

Mar. 24, 2010 (JP) .................................. 2010-068374

(51) Int. Cl.
*A61B 5/053* (2006.01)
*A61B 5/00* (2006.01)

(52) U.S. Cl.
CPC .............. *A61B 5/0537* (2013.01); *A61B 5/4872* (2013.01); *A61B 5/6823* (2013.01); *Y10T 29/49002* (2015.01)

(58) Field of Classification Search
CPC ... A61B 5/0537; A61B 5/6823; A61B 5/4872
USPC .......................................... 600/382, 390, 547
See application file for complete search history.

(56) References Cited

U.S. PATENT DOCUMENTS

| 7,283,869 B2 | 10/2007 | Onda et al. |
| 7,925,340 B2 | 4/2011 | Masuo et al. |
| 2004/0077969 A1 | 4/2004 | Onda et al. |

(Continued)

FOREIGN PATENT DOCUMENTS

| EP | 1621131 A1 | 2/2006 |
| EP | 1712179 A2 | 10/2006 |

(Continued)

OTHER PUBLICATIONS

Chinese Office Action issued in Chinese Patent Application No. 201180011501.4 dated Mar. 21, 2014, with English translation, 45 pgs.

(Continued)

*Primary Examiner* — Lee S Cohen
(74) *Attorney, Agent, or Firm* — McDermott Will & Emery LLP

(57) ABSTRACT

A body fat measurement apparatus is disclosed. The apparatus includes a current-applying electrode pair including two electrodes for applying a current, and a voltage-measuring electrode pair including two electrodes for measuring a voltage. The current-applying electrode pair is provided in such a way that a line which joins the two current-applying electrodes is inclined with respect to a trunk axis of a body to be measured. The voltage-measuring electrode pair is provided between the two current-applying electrodes.

10 Claims, 9 Drawing Sheets

(56) References Cited

U.S. PATENT DOCUMENTS

2006/0025701 A1 2/2006 Kasahara
2006/0235327 A1 10/2006 Masuo et al.
2009/0247896 A1* 10/2009 Kanai et al. .................. 600/547

FOREIGN PATENT DOCUMENTS

| EP | 1935338 | A1 | 6/2008 |
| EP | 1989999 | A1 | 11/2008 |
| JP | 2002-369806 | A | 12/2002 |
| JP | 2006-304999 | A | 11/2006 |
| JP | 2009-225854 | A | 10/2009 |
| WO | WO-2007/043271 | A1 | 4/2007 |

OTHER PUBLICATIONS

International Search Report mailed Aug. 28, 2011 issued in corresponding International Application No. PCT/JP2011/057090.

* cited by examiner

APPARATUS FOR MEASURING BODY FAT

RELATED APPLICATIONS

This application is the U.S. National Phase under 35 U.S.C. §371 of International Application No. PCT/JP2011/057090, filed on Mar. 24, 2011, which in turn claims the benefit of Japanese Application No. 2010-068374, filed on Mar. 24, 2010, the disclosures of which Applications are incorporated by reference herein.

TECHNICAL FIELD

The present invention relates to a body fat measurement apparatus.

BACKGROUND ART

A conventional body fat measurement apparatus measures body fat 80 (subcutaneous fat 81 and visceral fat 82) included in a cross section defined by electrodes arranged around a measured body 70 illustrated in FIG. 5A (e.g., refer to Patent Document 1).

PRIOR ART DOCUMENT

Patent Document

Patent Document 1: Japanese Laid-Open Patent Application No. 2002-369806

SUMMARY OF THE INVENTION

Problems that are to be Solved by the Invention

As illustrated in FIG. 5B, the body fat 80 is distributed three-dimensionally in fact. Although a conventional body fat measurement apparatus provides a measurement result reflecting the body fat along the cross section of FIG. 5A, it is difficult to measure the volume of the body fat accurately.

It is an object of the present invention to provide a body fat measurement apparatus that can measure the volume of the body fat accurately.

Means for Solving the Problem

A body fat measurement apparatus according to one aspect of the present invention includes a current-applying electrode pair including a first current-applying electrode and a second current-applying electrode, and a voltage-measuring electrode pair including a first voltage-measuring electrode and a second voltage-measuring electrode. The current-applying electrode pair is arranged so that a line connecting the first current-applying electrode with the second current-applying electrode is inclined with respect to a body axis of a measured body. The voltage-measuring electrode pair is arranged between the first current-applying electrode and the second current-applying electrode.

In one example, the first current-applying electrode is arranged on a left half of the measured body, and the second current-applying electrode is arranged on a right half of the measured body.

In one example, the body fat measurement apparatus includes a plurality of current-applying electrode pairs and the current-applying electrode pair is one of the plurality of current-applying electrode pairs. Positions of the plurality of current-applying electrode pairs are determined so that the middle position of each current-applying electrode pair coincides with a navel position of the measured body.

In one example, the body fat measurement apparatus includes a plurality of voltage-measuring electrode pairs arranged along a body axis, and the voltage-measuring electrode pair is one of the plurality of voltage-measuring electrode pairs.

In one example, the body fat measurement apparatus further includes a third current-applying electrode. The first current-applying electrode and the second current-applying electrode form a current-applying electrode pair. The first current-applying electrode and the third current-applying electrode form another current-applying electrode pair.

In one example, the body fat measurement apparatus further includes a movable part for moving the voltage-measuring electrodes on the measured body.

In one example, the body fat measurement apparatus includes a support member for attachment to the measured body. The current-applying electrode pair and the voltage-measuring electrode pair are supported by the support member.

In one example, the support member includes a belt for fixing the current-applying electrode pair and the voltage-measuring electrode pair to the measured body by fastening the current-applying electrode pair and the voltage-measuring electrode pair around the measured body.

In one example, the support member includes disposing parts for detachably attaching the current-applying electrode and the voltage-measuring electrode.

In one example, the body fat measurement apparatus includes a mark which indicates a reference position corresponding to a navel, a hipbone, or a backbone of the measured body to set the positions of the current-applying electrode pair and the voltage-measuring electrode pair.

In one example, the body fat measurement apparatus includes a computing circuit for calculating a volume of body fat based on a voltage measured by the voltage-measuring electrode pair.

In one example, the body fat measurement apparatus includes a display unit for displaying three-dimensional distribution of body fat based on the voltage measured by the voltage-measuring electrode pair.

A body fat measurement apparatus according to a further aspect of the present invention includes a current-applying electrode pair including a first current-applying electrode and a second current-applying electrode, a voltage-measuring electrode pair including a first voltage-measuring electrode and a second voltage-measuring electrode, and an elongated support member. The first current-applying electrode and the second current-applying electrode are supported by the support member on a straight line inclined with respect to a longitudinal axis of the support member and the voltage-measuring electrode pair is supported by the support member between the first current-applying electrode and the second current-applying electrode.

In one example, the first current-applying electrode, the second current-applying electrode, the first voltage-measuring electrode, and the second voltage-measuring electrode are aligned on a common straight line inclined with respect to the longitudinal axis of the support member.

In one example, the first current-applying electrode and the second current-applying electrode are arranged on a first straight line inclined with respect to the longitudinal axis of the support member. The first voltage-measuring electrode and the second voltage-measuring electrode are arranged on a second straight line intersecting the first straight line.

In one example, the support member is configured to fix the body fat measurement apparatus to the measured body. When the visceral fat measurement apparatus is fixed to the measured body by the support member, the current-applying electrode pair is positioned on the support member so that a line connecting the first current-applying electrode with the second current-applying electrode is inclined with respect to a body axis of the measured body.

In one example, the support member is a flexible support member that can be wound around the measured body.

A further aspect of the present invention provides a manufacturing method for a body fat measurement apparatus. The method includes supporting, with the support member, the first current-applying electrode and the second current-applying electrode on the straight line inclined with respect to the longitudinal axis of the support member, and supporting, with the support member, the voltage-measuring electrode pair between the first current-applying electrode and the second current-applying electrode.

In one example, the body fat measurement apparatus includes a support member having a longitudinal axis. The first current-applying electrode and the second current-applying electrode are supported by the support member on a straight line inclined with respect to the longitudinal axis of the support member. The first voltage-measuring electrode and the second voltage-measuring electrode are supported by the support member between the first current-applying electrode and the second current-applying electrode.

A further aspect of the present invention provides a body fat measurement apparatus that measures a body fat by measuring voltage of a measured body when current is applied to the measured body. The body fat measurement apparatus includes a current-applying electrode pair including a first current-applying electrode and a second current-applying electrode, a voltage-measuring electrode pair including a first voltage-measuring electrode and a second voltage-measuring electrode, and an elongated support member. The first current-applying electrode and the second current-applying electrode are supported by the support member on a straight line inclined with respect to a longitudinal axis of the support member. The voltage-measuring electrode pair is supported by the support member between the first current-applying electrode and the second current-applying electrode.

In one example, the first current-applying electrode, the second current-applying electrode, the first voltage-measuring electrode, and the second voltage-measuring electrode are aligned on a common straight line inclined with respect to the longitudinal axis of the support member.

In one example, the first current-applying electrode and the second current-applying electrode are supported by the support member on a first straight line inclined with respect to the longitudinal axis of the support member, and the first voltage-measuring electrode and the second voltage-measuring electrode are supported by the support member on a second straight line intersecting the first straight line.

In one example, the support member is configured to fix the body fat measurement apparatus to the measured body. When the visceral fat measurement apparatus is fixed to the measured body by the support member, the current-applying electrode pair is supported by the support member at a position determined so that a line connecting the first current-applying electrode with the second current-applying electrode is inclined with respect to a body axis of the measured body.

In one example, the support member is a flexible support member that can be wound around the measured body.

A further aspect of the present invention provides a manufacturing method for the body fat measurement apparatus. The method includes supporting, with the support member, the first current-applying electrode and the second current-applying electrode on the straight line inclined with respect to the longitudinal axis of the support member, and supporting, with the support member, the voltage-measuring electrode pair between the first current-applying electrode and the second current-applying electrode.

Effect of the Invention

The present invention provides a body fat measurement apparatus, which can measure the volume of the body fat accurately.

EMBODIMENTS OF THE INVENTION

First Embodiment

A first embodiment of the present invention is described with reference to FIG. 1 to FIG. 6.

Figure 1:
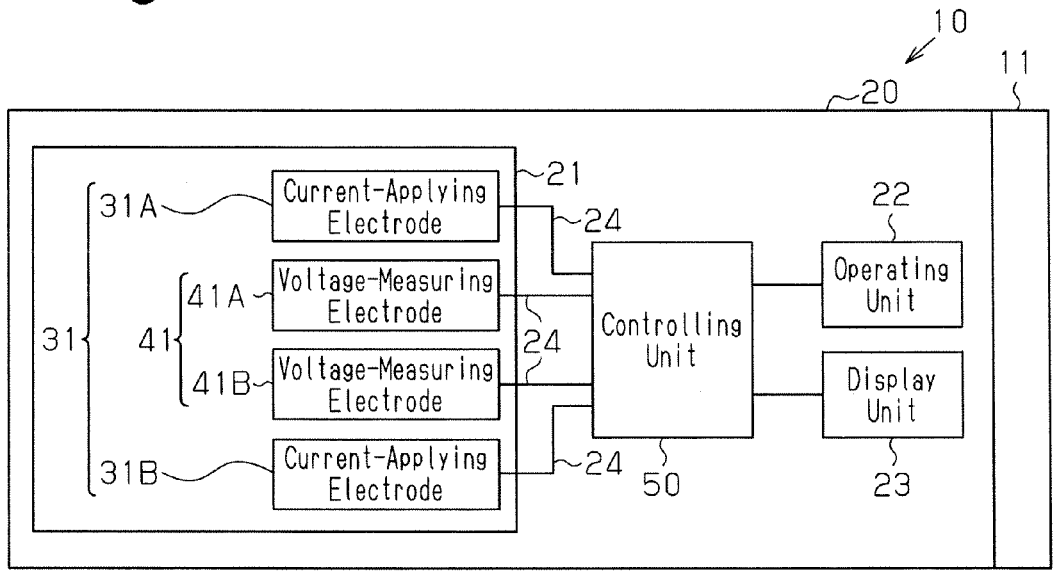
FIG. 1 is a block diagram of a body fat measurement apparatus according to a first embodiment of the present invention.

As illustrated in FIG. 1, a body fat measurement apparatus 10 includes a measuring part 20 for measuring body fat, and a belt 11 for winding the apparatus 10 around the measured body 70 and fixing the apparatus 10 to the measured body 70. The measured body 70 may be a human body illustrated in FIG. 3.

The measuring part 20 includes a detection plane 21 including a plurality of electrodes for detecting voltage by applying current to the measured body 70, an operating unit 22 like an input panel, a display unit 23 for displaying various information, and a controlling unit 50 connected to the electrodes of the detection plane 21.

The plurality of electrodes of the detection plane 21 includes a current-applying electrode pair 31 for applying current to the measured body 70, and a voltage-measuring electrode pair 41 for measuring the voltage of the measured body 70. The current-applying electrode pair 31 includes two current-applying electrodes 31A and 31B. The voltage-measuring electrode pair includes two voltage-measuring electrodes 41A and 41B. The current-applying electrodes 31A and 31B and the voltage-measuring electrodes 41A and 41B are connected to the controlling unit 50 through transmission lines 24. The current-applying electrodes 31A and 31B apply current to the measured body 70 in accordance with a control signal or a drive signal supplied from the controlling unit 50, and the voltage-measuring electrodes 41A and 41B provide measurement signals corresponding to the measured voltage of the measured body 70 to the controlling unit 50.

The operating unit 22 can provide information on the measured body 70, such as the constitution of the measured body 70, to the controlling unit 50 in accordance with the operation of a measurer, for example. The operating unit 22 can provide a signal for starting the measurement of body fat in response to the operation of a measurer. In this case, the controlling unit 50 starts the application of current by controlling the current-applying electrode pair 31. The voltage-measuring electrode pair 41 measures the voltage value of the measured body 70, and transmits the measurement signal corresponding to the measured voltage value to the controlling unit 50. The controlling unit 50 calculates the body fat amount, especially the volume of visceral fat, based on the measured voltage value (measurement signal) and the information on the measured body and the like that are input via the operating unit 22, and displays the calculated body fat amount on the display unit 23. In an example, the controlling unit 50 creates a three-dimensional image representing the distribution of visceral fat based on the measured voltage value, the information on the measured body such as abdominal circumference, age, and sex input via the operating unit 22, other parameters, and computer algorithm, and displays the image on the display unit 23. The controlling unit 50 functions as a computing circuit.

Figure 2A:
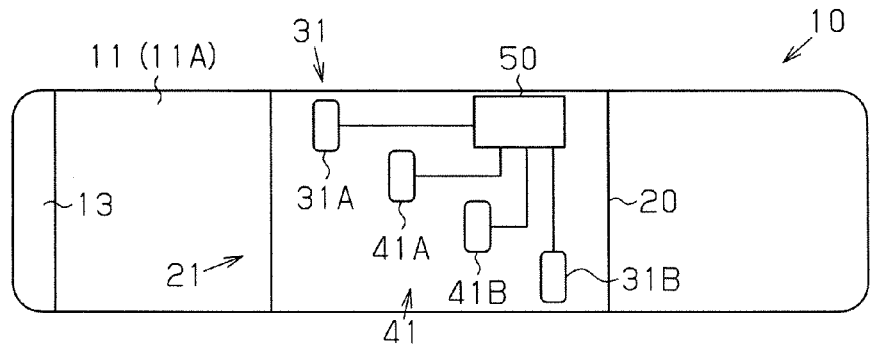
FIGS. 2A and 2B are a rear view and a front view of the body fat measurement apparatus of FIG. 1, respectively.
Figure 2B:
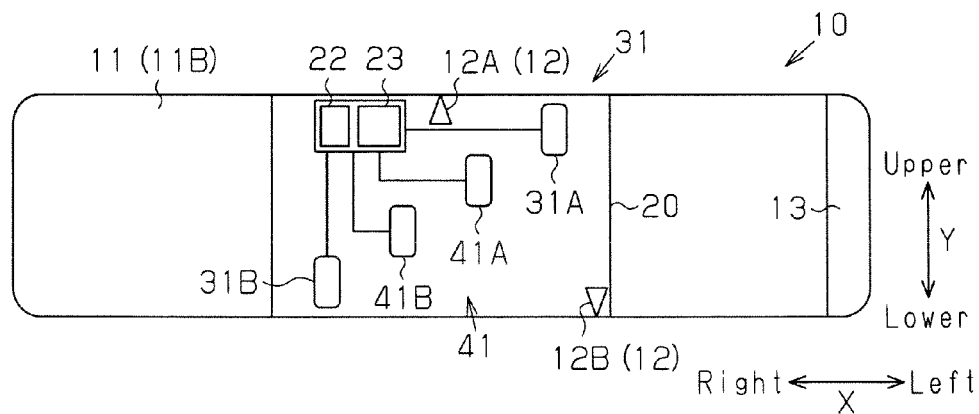

With reference to FIGS. 2, the structure of the body fat measurement apparatus 10 is described. The body fat measurement apparatus 10 includes a rear surface 11A illustrated in FIG. 2A and a front surface 11B illustrated in FIG. 2B. The rear surface 11A faces the measured body 70 when the body fat measurement apparatus 10 is wound around the measured body 70. The rear surface 11A is provided with the detection plane 21. The front surface 11B is opposite to the rear surface 11A. In the description below, the longitudinal direction of the body fat measurement apparatus 10 may be referred to as "horizontal direction X". In a state that the body fat measurement apparatus 10 is wound around the measured body 70, parts of the body fat measurement apparatus 10 corresponding to the right half and the left half of a body may be referred to as a right side and a left side, respectively. A direction orthogonal to the horizontal direction X may be referred to as "vertical direction Y". In the state that the body fat measurement apparatus 10 is wound around the measured body 70, a side thereof close to the top of the head of the measured body 70 may be referred to as an upper side.

As illustrated in FIGS. 2A and 2B, the body fat measurement apparatus 10 includes a support member for supporting the electrodes. The support member may be the belt 11 wound around the measured body 70 in close contact. The belt 11 has both ends at locations extended in the horizontal direction X from the measuring part 20. The measuring part 20 may be a part of the belt 11. The belt 11 is an example of a flexible elongated support member that can be wound around the measured body.

An electrode surface of each electrode of the current-applying electrode pair 31 and the voltage-measuring electrode pair 41 is exposed to the detection plane 21. The electrode material may be a stainless steel or a resin material plated with metal. The measuring part 20 can incorporate a power supply used for the body fat measurement apparatus 10. As illustrated in FIG. 2B, the front surface 11B of the body fat measurement apparatus 10 is provided with a mark 12, the operating unit 22, and the display unit 23.

The mark 12 serves as a positioning mark used for attaching the measuring part 20 including the electrodes to the measured body 70, and may be two marks 12A and 12B, for example. In the illustrated example, one mark 12A is located at an upper end in a center of the measuring part 20, while the other mark 12B is located at a lower left end of the measuring part 20. The locations of the electrodes on the body fat measurement apparatus 10 may be determined based on the mark 12.

Fasteners 13 are provided at a right end part of the rear surface 11A and a left end part of the front surface 11B. By attaching the fasteners 13 of the front surface 11B and the rear surface 11A after the belt 11 is wound around the measured body 70, the body fat measurement apparatus 10 is fixed to the measured body 70.

The current-applying electrodes 31A and 31B and the voltage-measuring electrodes 41A and 41B are located at equal intervals on a straight line in the order of the electrode 31A, the electrode 41A, the electrode 41B, and the electrode 31B from the upper left end to the lower right end of the measuring part 20.

The more specific positions of the electrodes seen from the front surface 11B are briefly described below:

The electrode 31A is located at the left end part of the measuring part 20 in the horizontal direction X, and located at the upper end part of the measuring part 20 in the vertical direction Y;

The electrode 31B is located at the right end part of the measuring part 20 in the horizontal direction X, and located at the lower end part of the measuring part 20 in the vertical direction Y;

The electrode 41A is located closer to the electrode 31A between the electrode 31A and the electrode 31B in the horizontal direction X, and located closer to the electrode 31A between the electrode 31A and the electrode 31B in the vertical direction Y; and The electrode 41B is located on the left side as compared with the electrode 41A between the electrode 31A and the electrode 31B in the horizontal direction X, and located below the 41A between the electrode 31A and the electrode 31B in the vertical direction Y.

In this manner, the voltage-measuring electrodes 41A and 41B are located between the current-applying electrodes 31A and 31B in the horizontal direction X. The voltage-measuring electrodes 41A and 41B are also located between the current-applying electrodes 31A and 31B in the vertical direction Y.

Figure 3:
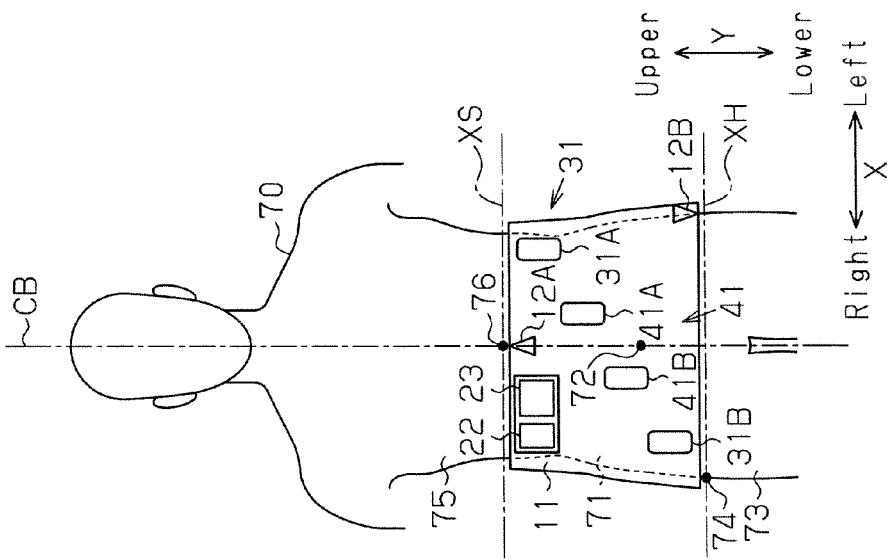
FIG. 3 is a schematic view of a body fat measurement apparatus before attachment to a measured body.
Figure 4:
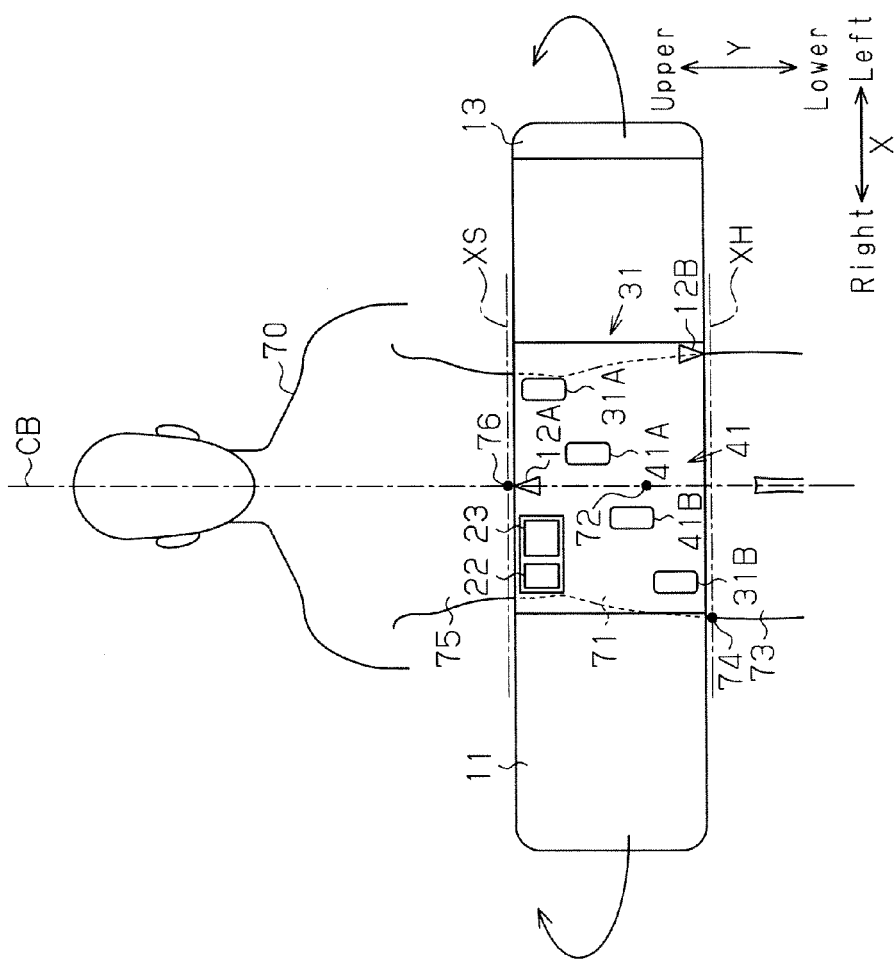
FIG. 4 is a schematic view of a body fat measurement apparatus attached to a measured body.

With reference to FIG. 3 and FIG. 4, the procedure of attaching the body fat measurement apparatus 10 to the measured body 70 is described.

Here, the longitudinal axis of a body trunk of the measured body 70 is defined as "body trunk axis CB". A plane passing through a breastbone lower end part 76, which is a lower end of a breast part 75, and intersecting with the body trunk axis CB perpendicularly is defined as "breastbone plane XS". A plane passing through a hipbone part 74, which is an ilium ridge part where a hipbone protrudes at an upper end of a hip part 73, and being orthogonal to the body trunk axis CB is defined as "hipbone plane XH". The right half and the left half of the body correspond to the parts more on the right and left sides than the breastbone lower end part 76, respectively.

As illustrated in FIG. 3, the rear surface 11A of the belt 11 is attached to an abdominal part 71 of the measured body 70 (see FIG. 2A), and the position of the mark 12A in the horizontal direction X is aligned at the breastbone lower end part 76. The position of the mark 12A in the vertical direction Y is aligned at the breastbone plane XS or below the plane XS. The position of the mark 12B is aligned at the breastbone part 74. The position of the mark 12B in the vertical direction Y is aligned at the hipbone plane XH or slightly upper than the plane XH. The belt 11 is wound around the measured body 70 and the body fat measurement apparatus 10 is fixed to the measured body 70 with the fastener 13.

As illustrated in FIG. 4, when the belt 11 is wound around the abdominal part 71 of the measured body 70, the current-applying electrode pair 31 and the voltage-measuring electrode pair 41 are in contact with a body surface of the measured body 71. In this manner, by winding the belt 11 around the measured body 70, the current-applying electrode pair 31 and the voltage-measuring electrode pair 41 are arranged inclined with respect to the body axis of the measured body 70 automatically. When a measurer operates the operating unit 22 in this state, the measurement of the body fat is started.

Figure 5A:
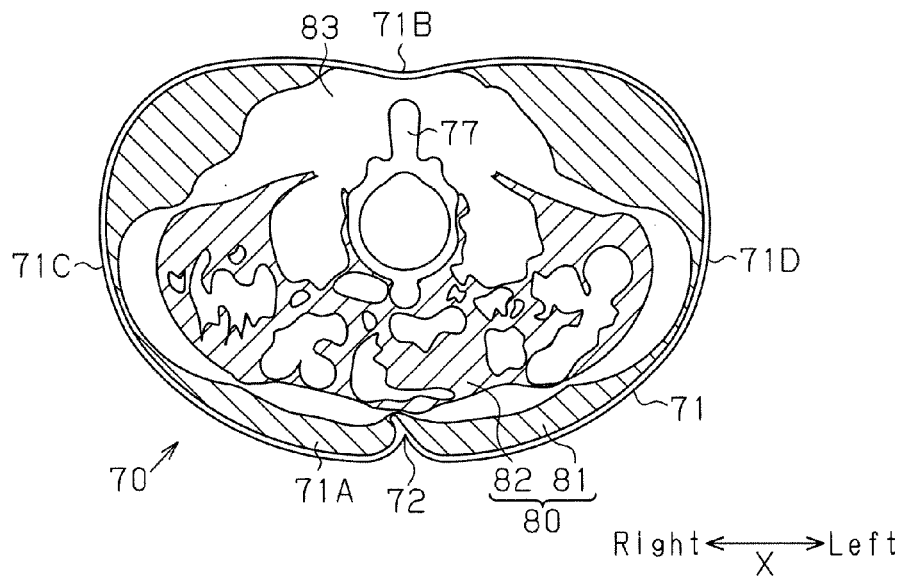
FIGS. 5A and 5B are a schematic sectional view and a partial cutaway perspective view of a measured body, respectively.
Figure 5B:
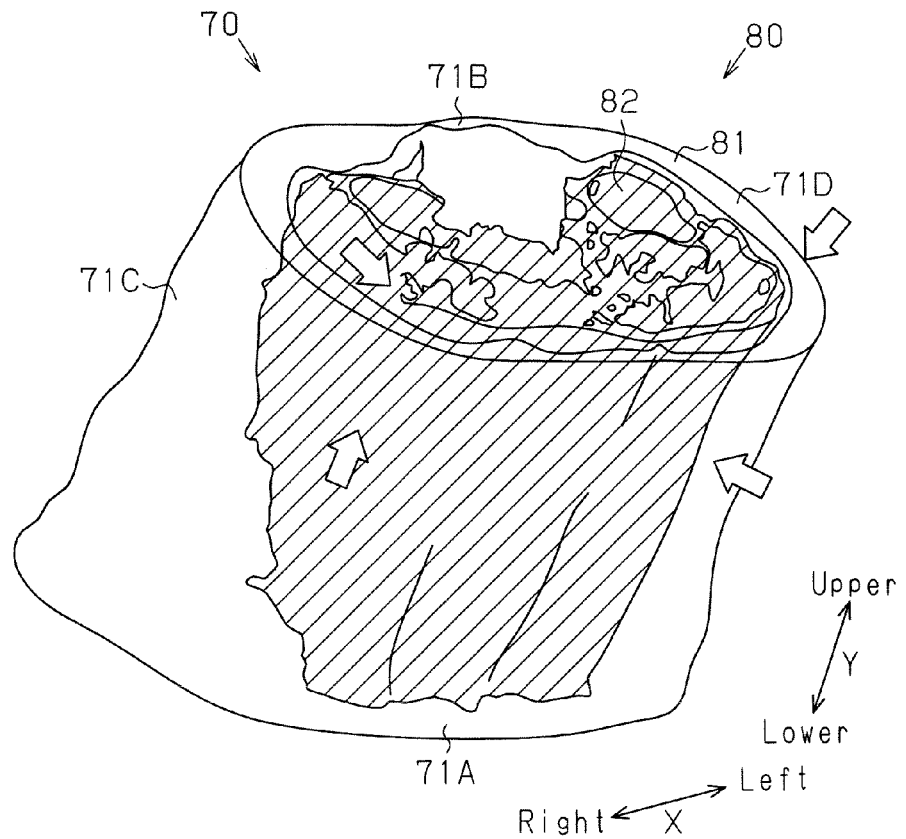

With reference to FIGS. 5, the structure of body fat 80 of the measured body 70 of the body fat measurement apparatus 10 is described. FIG. 5A illustrates the distribution of the body fat 80 of a cross section perpendicular to the body trunk axis CB passing through a navel of the measured body 70, and FIG. 5B illustrates the three-dimensional distribution of the body fat 80 ranging from the breastbone plane XS to the hipbone plane XH of the measured body 70. Note that the hatching pattern of FIG. 5A indicates the distribution of the body fat 80 including the subcutaneous fat 81 and the visceral fat 82. The hatching pattern of FIG. 5B indicates the distribution of the visceral fat 82.

FIG. 5A corresponds to the cross section orthogonal to the body trunk axis CB at the height of a navel 72 of the measured body 70. The subcutaneous fat 81 exists in a layer form around the periphery below the body surface of the measured body 70. The layer of the subcutaneous fat 81 is thick in a front part 71A and a rear part 71B, and is relatively thin in a left flank 71D and a right flank 71C. The visceral fat 82 exists between the internal organs in the abdominal cavity. In general, the body fat 80 is distributed approximately symmetrically in the right half and left half of the body with respect to a backbone 77.

As indicated by arrow in FIG. 5B, the volume of the body fat 80 is different depending on the height in the measured body 70, that is, for each cross-sectional position orthogonal to the body trunk axis CB. For example, the visceral fat 82 is much distributed particularly in the right and left sides of the front part 71A of the abdominal part 71.

Figure 6:
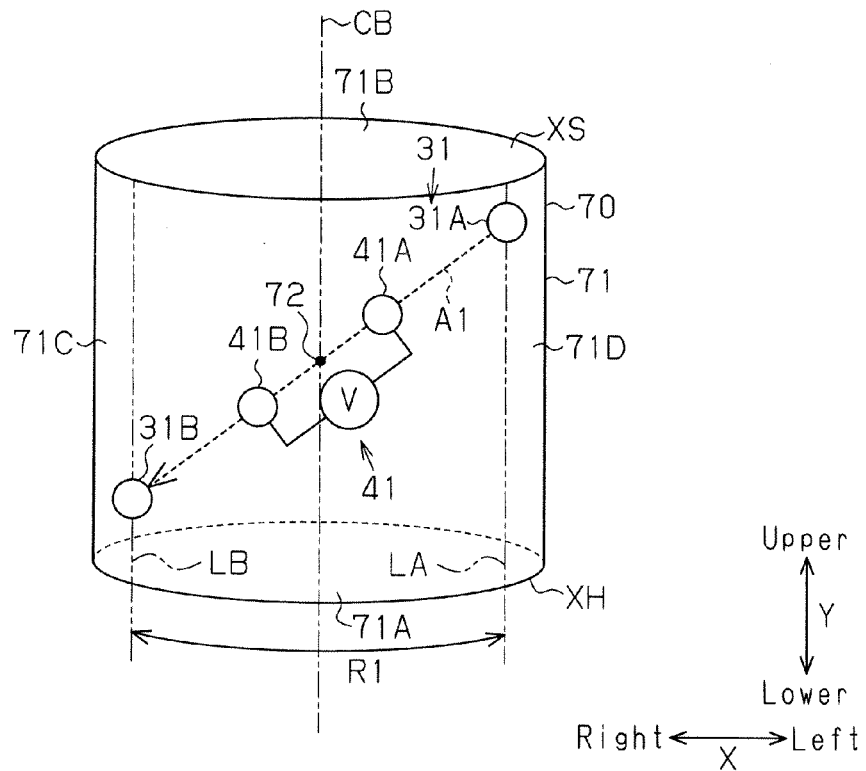
FIG. 6 is a schematic view indicating the positions of electrodes in a body fat measurement apparatus attached to a measured body.

With reference to FIG. 6, the summary of arrangement of the current-applying electrode pair 31 and the voltage-measuring electrode pair 41 for the measured body 70 and a method for measuring the body fat 80 is described. A cylindrical shape of FIG. 6 indicates the abdominal part 71 of FIG. 4 around which the body fat measurement apparatus 10 is wound.

Hereinafter, a line connecting the current-applying electrode 31A with the current-applying electrode 31B is defined as "inter-electrode line A1". A line which passes through the current-applying electrode 31A and is in parallel to the body trunk axis CB is defined as a reference line LA. A line which passes through the current-applying electrode 31B and is in parallel to the body trunk axis CB is defined as a reference line LB.

The current-applying electrode 31A and the current-applying electrode 31B are provided for the left half and right half of the body via the body trunk axis CB, respectively. In an example, the current-applying electrode 31A is arranged in the vicinity of the left flank 71D and below the breastbone plane XS. The current-applying electrode 31B is arranged in the vicinity of the right flank 71C and over the hipbone plane XH.

Here, the body surface around the abdominal part 71 and the hip part 73 is cut along a line parallel to the body trunk axis CB in the center of the rear part 71B, and a development view in which this is developed into a plan view is assumed.

In the development view, the inter-electrode line A1 is inclined with respect to the body trunk axis CB. In other words, the current-applying electrodes 31A and 31B are located at positions different from each other in the horizontal direction X and the vertical direction Y.

When the range between the reference line LA and the reference line LB in the development view is defined as "inter-electrode range R1", the arrangement of the voltage-measuring electrode pair 41 can be explained as below.

The voltage-measuring electrode pair 41 is arranged in the inter-electrode range R1 in the development view. That is, the voltage-measuring electrodes 41A and 41B are arranged in the inter-electrode range R1. Each electrode 41A and 41B is arranged on the inter-electrode line A1. The middle position of the voltage-measuring electrode pair 41 coincides with the middle position of the current-applying electrode pair 31.

Next, measurement of the body fat 80 is described.

The current fed from the current-applying electrode 31A to the current-applying electrode 31B flows inside the measured body 70 in the state that the current is inclined with respect to the body trunk axis CB. When the current flows inside the measured body 70, the voltage changes depending on the composition of the measured body 70. The change in voltage is different depending on the resistance values of the subcutaneous fat 81, the visceral fat 82, and a muscle 83.

When the measurement of the body fat 80 is started, the current flows between the current-applying electrodes 31A and 31B located at the different heights. The voltage value when the current flows obliquely inside the measured body 70 is measured by the voltage-measuring electrodes 41A and 41B. Based on the measured voltage value, the controlling unit 50 calculates the amount, i.e., the volume of the body fat 80, especially the volume of the visceral fat 82, between the electrodes 31A and 31B and in the vicinity of the electrodes 31A and 31B and displays the calculated result on the display unit 23. Since various known methods can be employed as a calculation method for the volume of the body fat, the description is omitted.

As described above, the present embodiment can provide the following effects.

(1) In the present embodiment, the current-applying electrode pair 31 is provided so that the line connecting current-applying electrodes 31A and 31B with each other is inclined with respect to the body trunk axis CB of the measured body 70 and the voltage-measuring electrode pair 41 is provided between the current-applying electrode 31A and the current-applying electrode 31B. Therefore, the voltage-measuring electrode pair 41 measures the voltage when the current flows obliquely between the positions at the different heights in the measured body 70. This makes it possible to measure the volume of the body fat 80 accurately. Moreover, the voltage can be detected with high sensitivity as compared with the case in which the voltage-measuring electrode pair 41 is provided outside between the electrode 31A and the electrode 31B.

(2) In the present embodiment, the current-applying electrode 31A and the current-applying electrode 31B are arranged on the left half and right half of the measured body 70, respectively. That is, the electrode pair 31 is arranged over the center of the measured body 70; therefore, the measurement results reflecting the volume of the body fat 80 of the left half and right half of the body can be obtained.

(3) In the present embodiment, the belt 11 is provided with the current-applying electrode pair 31 and the voltage-measuring electrode pair 41; therefore, the positional relation between the electrodes of the current-applying electrode pair 31 and the voltage-measuring electrode pair 41 does not change for every measurement of the body fat 80 and the variation in measurement result of the body fat 80 can be reduced.

(4) The body fat measurement apparatus 10 includes the belt 11 for fixing the measuring part 20 to the measured body 70. Therefore, the displacement of the electrode pairs 31 and 41 with respect to the measured body 70 can be reduced as compared with the case of measuring the body fat 80 while a measurer holds the measuring part 20 with a hand. Moreover, since the measurer does not have to hold the measuring part 20 with a hand for measuring the body fat 80, the burden on the measurer can be decreased.

(5) The body fat measurement apparatus 10 includes the mark 12B indicating the reference position corresponding to the hipbone part 74 of the measured body 70. The positions of the current-applying electrode pair 31 and the voltage-measuring electrode pair 41 are set based on the mark 12B. Therefore, it is possible to suppress the large difference in position of the current-applying electrode pair 31 and the voltage-measuring electrode pair 41 for each measurement of the body fat 80, which allows the appropriate measurement on change over time of the body fat 80 on the same part of the measured body 70.

(6) The controlling unit 50 calculates the volume of the body fat 80 including the subcutaneous fat 81 and the visceral fat 82 based on the voltage measured by the voltage-measuring electrode pair 41. Thus, a measurer can know the volume of the body fat 80 of each part of the measured body 70.

(7) The body fat measurement apparatus 10 includes the display unit 23 for displaying the three-dimensional distribution of the body fat 80 including the subcutaneous fat 81 and the visceral fat 82. Therefore, a measurer can visually recognize the stereoscopic distribution of the body fat 80.

(8) As illustrated in FIG. 5B, in general, the visceral fat 82 mostly exists in the range (approximately 20 cm) from the vicinity of the breastbone plane XS to the vicinity of the hipbone plane XH. By disposing the current-applying electrode 31A below the breastbone plane XS and in the left flank 71D and disposing the current-applying electrode 31B above the hipbone plane XH and in the right flank 71C, the measurement results reflecting the amount of the visceral fat 82 of the measured body 70 can be obtained.

Second Embodiment

Figure 7:
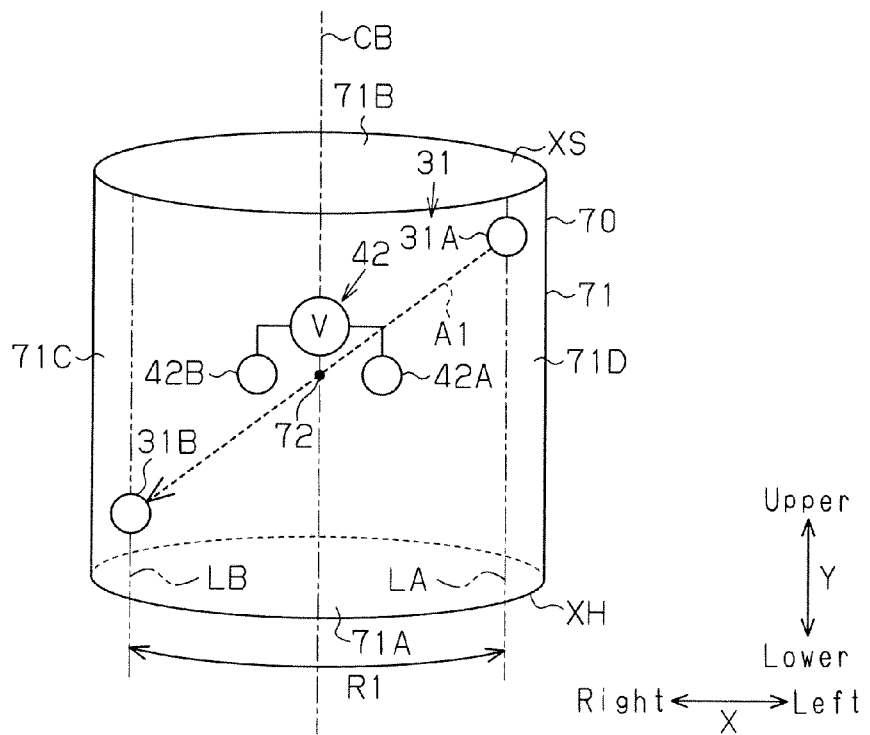
FIG. 7 is a schematic view indicating the positions of electrodes in a body fat measurement apparatus according to a second embodiment of the present invention.

With reference to FIG. 7, a point of the second embodiment of the present invention that is different from the first embodiment is described. The second embodiment is different from the first embodiment in the arrangement of the voltage-measuring electrodes. The other points are similar to those in the first embodiment; therefore, the similar structures are denoted by the same reference symbols and description thereof is omitted.

As illustrated in FIG. 7, a voltage-measuring electrode pair 42 includes voltage-measuring electrodes 42A and 42B. The voltage-measuring electrode pair 42 is arranged in the inter-electrode range R1. The middle position of the electrode pair 42 coincides with the middle position of the current-applying electrode pair 31. In an example, a line connecting the electrodes 42A and 42B with each other is substantially parallel to the breastbone plane XS and the hipbone plane XH. The inter-electrode line A1 passes above the voltage-measuring electrode 42A and below the voltage-measuring electrode 42B.

As described above, the present embodiment can provide the effects similar to those of the first embodiment.

Third Embodiment

Figure 8:
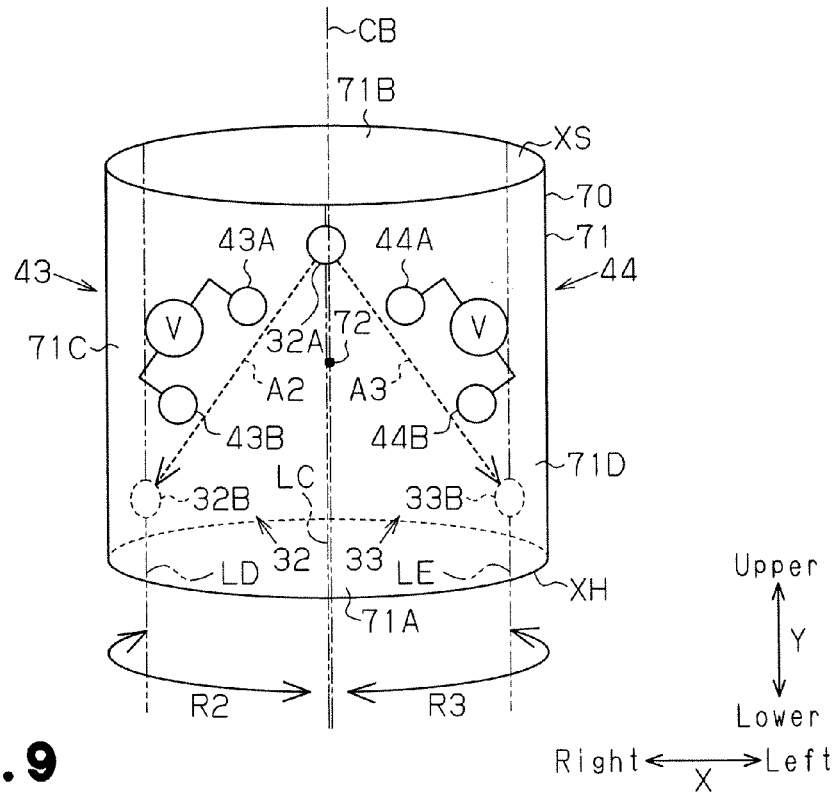
FIG. 8 is a schematic view indicating the positions of electrodes in a body fat measurement apparatus according to a third embodiment of the present invention.

With reference to FIG. 8, a point of the third embodiment of the present invention that is different from the first embodiment is described. The third embodiment is different from the first embodiment in the arrangement of the current-applying electrodes and the voltage-measuring electrodes. The other points are similar to those in the first embodiment; therefore, the similar structures are denoted by the same reference symbols and description thereof is omitted.

As illustrated in FIG. 8, the body fat measurement apparatus 10 includes two current-applying electrode pairs 32 and 33 and two voltage-measuring electrode pairs 43 and 44.

The current-applying electrode pair 32 includes electrodes 32A and 32B. The current-applying electrode pair 33 includes electrodes 32A and 33B. The electrode 32A is shared between the two electrode pairs 32 and 33.

The electrode 32A is arranged below the breastbone plane XS and in the vicinity of the breastbone plane XS in the vicinity of the breastbone lower end part 76. The electrode 32B is located above the hipbone plane XH and in the vicinity of the hipbone plane XH and the rear part 71B near the right flank 71C (for example, 1 to 10 cm from the backbone 77). The electrode 33B is located above the hipbone plane XH and in the vicinity of the hipbone plane XH and the rear part 71B near the left flank 71D (for example, 1 to 10 cm from the backbone 77).

The voltage-measuring electrode pair 43 includes two voltage-measuring electrodes 43A and 43B arranged on the right half of the body. The voltage-measuring electrode pair 44 includes two voltage-measuring electrodes 44A and 44B arranged on the left half of the body.

A line connecting the current-applying electrode 32A with the current-applying electrode 32B is defined as "inter-electrode line A2" below. A line connecting the current-applying electrode 32A with the current-applying electrode 33B is defined as "inter-electrode line A3". A line passing through the current-applying electrode 32A and being in parallel to the body trunk axis CB is defined as a reference line LC. A line passing through the current-applying electrode 32B and being in parallel to the body trunk axis CB is defined as a reference line LD. A line passing through the current-applying electrode 33B and being in parallel to the body trunk axis CB is defined as a reference line LE.

Here, the body surface around the abdominal part 71 and the hip part 73 is cut along a line parallel to the body trunk axis CB in the center of the rear part 71B, and a development view in which this is developed into a plan view is assumed.

In the development view, the inter-electrode lines A2 and A3 are inclined with respect to the body trunk axis CB. In other words, the current-applying electrodes 32A and 32B are located at positions different from each other in the horizontal direction X and the vertical direction Y. Moreover, the current-applying electrodes 32A and 33B are located at positions different from each other in the horizontal direction X and the vertical direction Y. The current-applying electrodes 32B and 33B are located at the same position in the vertical direction Y. The distance from the current-applying electrode 32B to the navel 72 is equal to the distance from the current-applying electrode 33B to the navel 72. The electrodes 32B and 33B are symmetrical with respect to the navel 72.

When the range between the reference line LC and the reference line LD in the development view is defined as "inter-electrode range R2" and the range between the reference line LC and the reference line LD is defined as "inter-electrode range R3", the arrangement of the voltage-measuring electrode pairs 43 and 44 can be explained as below.

The voltage-measuring electrode pair 43 (electrodes 43A and 43B) is arranged in the inter-electrode range R2 in the development view. The middle position of the voltage-measuring electrode pair 43 coincides with the middle position of the current-applying electrode pair 32. In FIG. 8, the electrode 32B is in the rear part 71B of the measured body 70; therefore, it is noted that the middle position of the electrode pair 32 in the development view is displaced from the inter-electrode line A2.

The voltage-measuring electrode pair 44 (electrodes 44A and 44B) is arranged in the inter-electrode range R3 in the development view. The middle position of the voltage-measuring electrode pair 44 coincides with the middle position of the current-applying electrode pair 32. Since the electrode 33B is in the rear part 71B of the measured body 70 in FIG. 8, it is noted that the middle position of the electrode pair 33 in the development view is displaced from the inter-electrode line A3.

When the measurement of the body fat 80 is started, the controlling unit 50 first supplies current between the current-applying electrode pair 32 and then supplies current between the current-applying electrode pair 33. Based on the voltage value measured by the voltage-measuring electrode pairs 43 and 44, the controlling unit 50 calculates the amount or volume of the body fat 80 between the electrodes 32A and 32B, between the electrodes 32A and 33B, and in the vicinity of the electrodes 32A, 32B, and 33B, and displays the calculation results on the display unit 23. Note that the measurement voltage of the voltage-measuring electrode pair 43 reflects the body fat 80 of the right half of the body while the measurement voltage of the voltage-measuring electrode pair 44 reflects the body fat 80 of the left half of the body. The controlling unit 50 may calculate the amount or volume of the body fat 80 in the right half and left half of the body and display the amount or volume of the body fat 80 in the right half and left half of the body in the display unit 23.

As thus described above, the present embodiment can provide the following effects in addition to the effects similar to the above (1) and (3) to (8).

(9) The current-applying electrode pair 32 and the current-applying electrode pair 33 share the current-applying electrode 32A. Therefore, the number of electrodes can be reduced by one as compared with the case in which two current-applying electrode pairs are formed by four electrodes.

(10) As illustrated in FIG. 5, the visceral fat 82 is mostly distributed in the right front and left front parts. In the present embodiment, since the inter-electrode ranges R2 and R3 correspond to the right half and left half of the body, respectively, the amount of the visceral fat 82 in the left half and the right half of the body can be measured individually. Therefore, the relative balance on the amount of the visceral fat 82 between the left half and the right half of the body can be estimated.

(11) In the present embodiment, the two current-applying electrode pairs 32 and 33 are provided. This improves the accuracy of measuring the body fat 80 because the current can be supplied in multiple directions inside the measured body 70.

Fourth Embodiment

Figure 9:
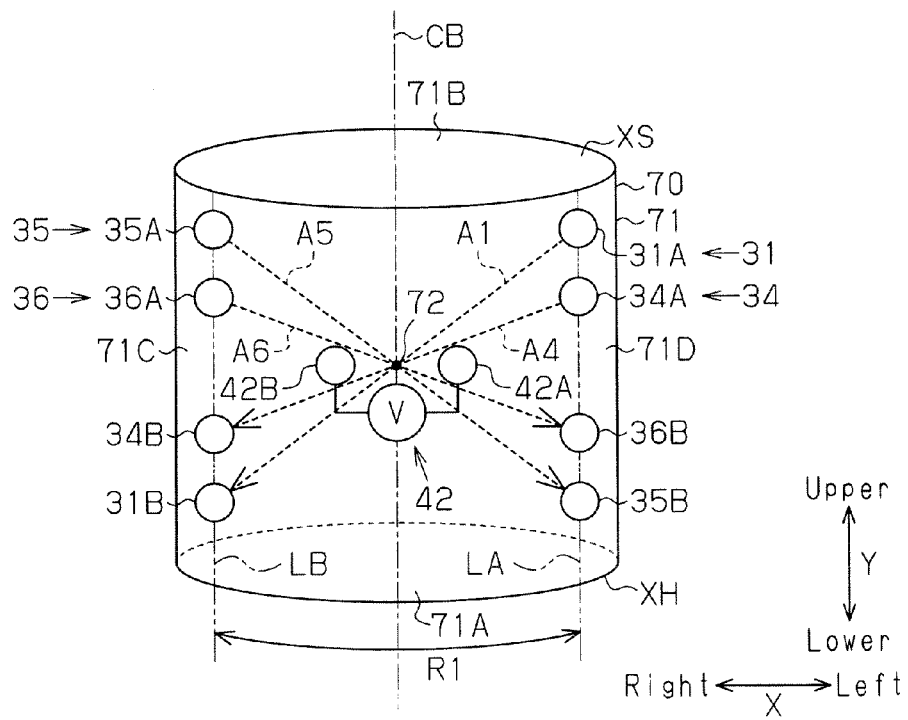
FIG. 9 is a schematic view indicating the positions of electrodes in a body fat measurement apparatus according to a fourth embodiment of the present invention.

With reference to FIG. 9, a point of the fourth embodiment of the present invention that is different from the first embodiment is described. The fourth embodiment is different from the first embodiment in the arrangement of the current-applying electrodes and the voltage-measuring electrodes. The other points are similar to those in the first embodiment; therefore, the similar structures are denoted by the same reference symbols and description thereof is omitted.

As illustrated in FIG. 9, the body fat measurement apparatus 10 includes four current-applying electrode pairs 31, 34, 35, and 36.

The current-applying electrode pair 31 includes the current-applying electrodes 31A and 31B. The current-applying electrode pair 34 includes current-applying electrodes 34A and 34B. The current-applying electrode pair 35 includes current-applying electrodes 35A and 35B. The current-applying electrode pair 36 includes current-applying electrodes 36A and 36B.

The current-applying electrodes 31A and 31B are provided for the left half and right half of the body, respectively. For example, the current-applying electrode 31A is arranged in the vicinity of the left flank 71D and below the breastbone plane XS. The current-applying electrode 31B is arranged in the vicinity of the right flank 71C and above the hipbone plane XH.

The current-applying electrodes 34A and 34B are provided inside the current-applying electrode pair 31 in the vertical direction Y. For example, the current-applying electrode 34A is arranged in the vicinity of the left flank 71D and the breastbone plane XS and below the electrode 31A. The current-applying electrode 34B is arranged in the vicinity of the right flank 71C and the hipbone plane XH and above the electrode 31B.

The current-applying electrodes 35A and 35B are provided symmetrically with respect to the navel 72 with the current-applying electrodes 31A and 31B. For example, the current-applying electrode 35A is arranged in the vicinity of the right flank 71C and below the breastbone plane XS. The current-applying electrode 35B is arranged in the vicinity of the left flank 71D and above the hipbone plane XH.

The current-applying electrodes 36A and 36B are provided symmetrically with respect to the navel 72 with the current-applying electrodes 34A and 34B inside the current-applying electrode pair 35 in the vertical direction Y. For example, the current-applying electrode 36A is arranged in the vicinity of the right flank 71C and the breastbone plane XS and below the current-applying electrode 35A. The current-applying electrode 36B is arranged in the vicinity of the left flank 71D and the hipbone plane XH and above the current-applying electrode 35B.

The positions of the electrodes 31A, 34A, 35B, and 36B in the horizontal direction X coincide with each other. The positions of the electrodes 31B, 34B, 35A, and 36A in the horizontal direction X coincide with each other. The middle position of each electrode pair 31, 34, 35, and 36 coincides with the position of the navel 72.

A line connecting the current-applying electrode 31A with the current-applying electrode 31B is defined as "inter-electrode line A1". A line connecting the current-applying electrode 34A with the current-applying electrode 34B is defined as "inter-electrode line A4". A line connecting the current-applying electrode 35A with the current-applying electrode 35B is defined as "inter-electrode line A5". A line connecting the current-applying electrode 36A with the current-applying electrode 36B is defined as "inter-electrode line A6". A line which passes through the current-applying electrodes 31A, 34A, 35B, and 36B and is in parallel to the body trunk axis CB is defined as a reference line LA. A line which passes through the current-applying electrode 31B, 34B, 35A, and 36A and is in parallel to the body trunk axis CB is defined as a reference line LB.

Here, the body surface around the abdominal part 71 and the hip part 73 is cut along a line parallel to the body trunk axis CB in the center of the rear part 71B, and a development view in which this is developed into a plan view is assumed.

In the development view, the inter-electrode lines A1, A4, A5, and A6 are inclined with respect to the body trunk axis CB. The two electrodes of each of the current-applying electrode pairs 31, 34, 35, and 36 are located at positions different from each other in the horizontal direction X and the vertical direction Y.

The voltage-measuring electrode pair 42 is arranged in the inter-electrode range R1. The middle position of the electrode pair 42 coincides with the middle position of each of the current-applying electrode pairs 31, 34, 35, and 36. In an example, a line connecting the electrodes 42A and 42B with each other is substantially parallel to the breastbone plane XS and the hipbone plane XH.

As described above, the present embodiment can provide the following effects in addition to the above effects (1) to (8) and (11).

(12) The current-applying electrode pairs 31, 34, 35, and 36 are provided so that their middle positions coincide with the position of the navel 72 of the measured body 70. Therefore, the volume of the body fat 80 around the navel 72 can be measured more accurately. For example, even though the measured bodies 70 have the same amount of the visceral fat 82, the measured body 70 having the visceral fat 82 mostly distributed in the part close to the surface layer and the measured body having the visceral fat 82 mostly distributed in the part away from the surface layer (the part close to the body axis) have different impedance detected. In this sense, when the current-applying electrode pairs 31, 34, 35, and 36 are provided to supply current in multiple directions to the one voltage-measuring electrode pair 42, whether the body fat 80, especially the visceral fat 82, is mostly distributed in the part close to the surface layer or in the part close to the body axis can be measured accurately.

Fifth Embodiment

Figure 10:
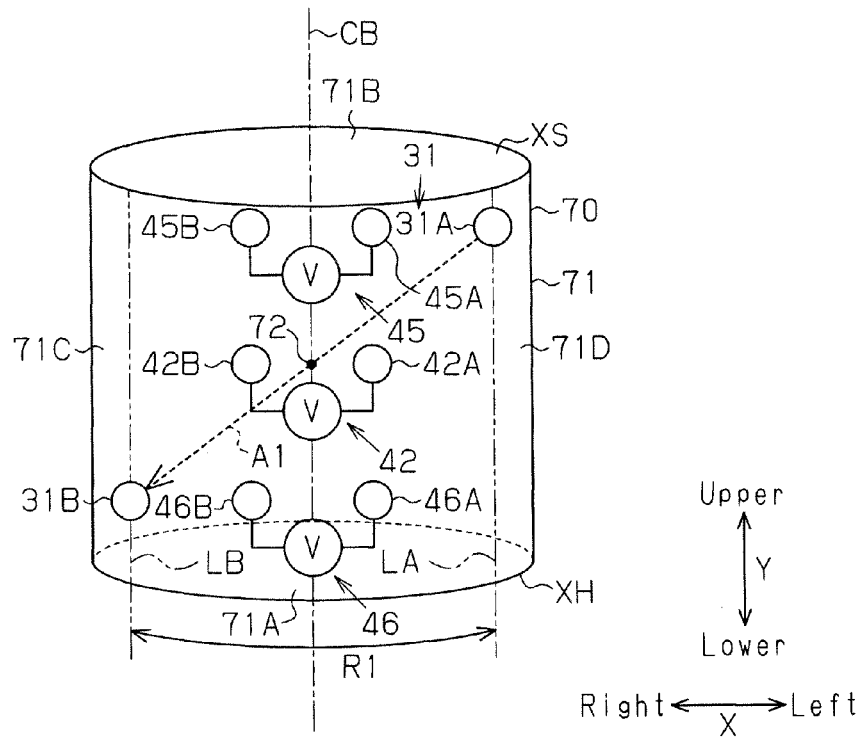
FIG. 10 is a schematic view indicating the positions of electrodes in a body fat measurement apparatus according to a fifth embodiment of the present invention.

With reference to FIG. 10, a point of the fifth embodiment of the present invention that is different from the first embodiment is described. The fifth embodiment is different from the first embodiment in the arrangement of the voltage-measuring electrodes. The other points are similar to those in the first embodiment; therefore, the similar structures are denoted by the same reference symbols and description thereof is omitted.

As illustrated in FIG. 10, the body fat measurement apparatus 10 includes three voltage-measuring electrode pairs 42, 45, and 46. The voltage-measuring electrode pair 42 includes the electrodes 42A and 42B. The voltage-measuring electrode pair 45 includes electrodes 45A and 45B. The voltage-measuring electrode pair 46 includes electrodes 46A and 46B.

The voltage-measuring electrodes 42A and 42B are provided for the left half and right half of the body, respectively. For example, the voltage-measuring electrodes 42A and 42B are provided on the left side and the right side of the navel 72 at the height of the navel 72 in the horizontal direction X.

The voltage-measuring electrodes 45A and 45B are provided for the left half and right half of the body, respectively above the voltage-measuring electrode pair 42. For example, the voltage-measuring electrodes 45A and 45B are arranged in the vicinity of the breastbone plane XS above the inter-electrode line A1 in the vertical direction Y and on the left side and right side of the body trunk axis CB in the horizontal direction X, respectively.

The voltage-measuring electrodes 46A and 46B are provided for the left half and right half of the body via the body trunk axis CB below the voltage-measuring electrode pair 42. For example, the voltage-measuring electrodes 46A and 46B are arranged in the vicinity of the hipbone plane XH below the inter-electrode line A1 in the vertical direction Y and on the left side and right side of the body trunk axis CB in the horizontal direction X, respectively.

The voltage-measuring electrode pairs 42, 45, and 46 are arranged in the inter-electrode range R1. The middle position of each of the voltage-measuring electrode pairs 42, 45, and 46 coincides with the middle position of the current-applying electrode pair 31. Lines connecting the two electrodes of the voltage-measuring electrode pairs 42, 45, and 46 may be substantially parallel to the breastbone plane XS and the hipbone plane XH.

As described above, the present embodiment can provide the following effects in addition to the above effects (1) to (8).

(13) The voltage-measuring electrode pairs 42, 45, and 46 are arranged along the body trunk axis CB. Therefore, voltage at various positions along the body trunk axis CB between the current-applying electrode pair 31 can be measured. This makes it possible to measure the volume of the body fat 80 more accurately.

(14) The voltage-measuring electrode pair 45 is arranged in the vicinity of the breastbone plane XS and the voltage-measuring electrode pair 46 is arranged in the vicinity of the hipbone plane XH. That is, the voltage-measuring electrode pairs 45 and 46 are arranged near an outer edge of a region where current flows. This makes it possible to measure the voltage including the voltage near the outer edge of the region where current flows; therefore, more accurate measurement becomes possible.

(15) The plurality of voltage-measuring electrode pairs 42, 45, and 46 is arranged between one current-applying electrode pair 31. Therefore, the combination of electrodes included in the electrode pair can be selected and switched in accordance with the purpose of measurement.

Sixth Embodiment

Figure 11:
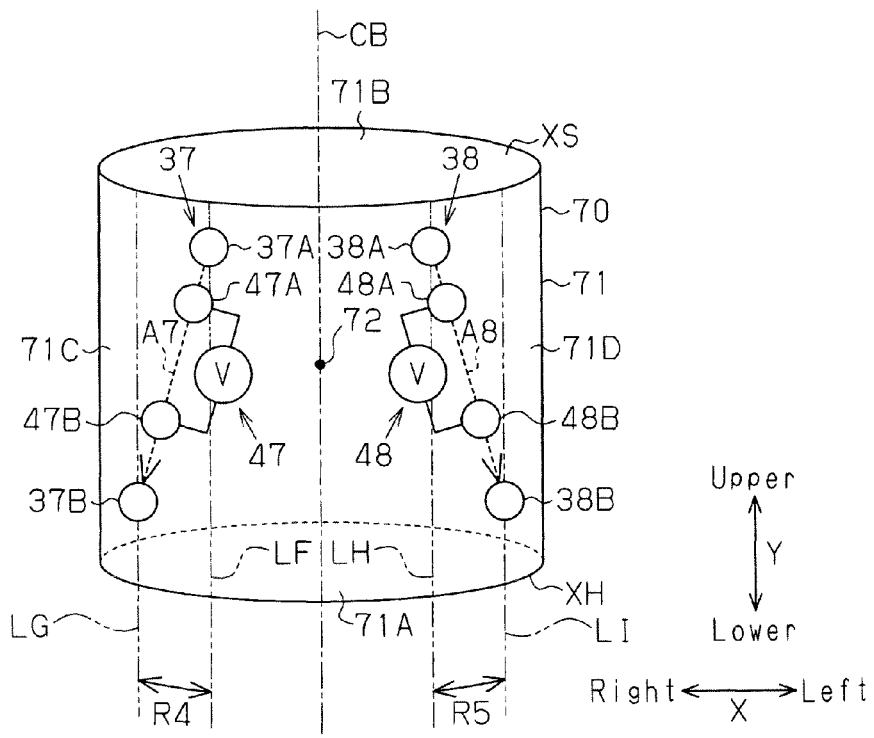
FIG. 11 is a schematic view indicating the positions of electrodes in a body fat measurement apparatus according to a sixth embodiment of the present invention.

With reference to FIG. 11, the sixth embodiment of the present invention is described. The sixth embodiment is different from the first embodiment in the arrangement of the current-applying electrodes and the voltage-measuring electrodes. The different point from that of the first embodiment is described. The other points are similar to those in the first embodiment; therefore, the similar structures are denoted by the same reference symbols and description thereof is omitted.

As illustrated in FIG. 11, the body fat measurement apparatus 10 includes two current-applying electrode pairs 37 and 38 and two voltage-measuring electrode pairs 47 and 48.

The current-applying electrode pair 37 includes current-applying electrodes 37A and 37B. The electrode 37A is arranged, on the right half of the body, in the vicinity of the breastbone lower end part 76, on the right side of the breastbone lower end part 76, in the vicinity of the breastbone plane XS, and below the breastbone plane XS. The electrode 37B is arranged, on the right half of the body, in the front part 71A close to the right flank 71C, in the vicinity of the hipbone plane XH, and above the hipbone plane XH.

The current-applying electrode pair 38 includes current-applying electrodes 38A and 38B. The electrode 38A is arranged, on the left half of the body, in the vicinity of the breastbone lower end part 76, on the left side of the breastbone lower end part 76, in the vicinity of the breastbone plane XS, and below the breastbone plane XS. The electrode 38B is arranged, on the left half of the body, in the front part 71A close to the left flank 71D, in the vicinity of the hipbone plane XH, and above the hipbone plane XH.

The voltage-measuring electrode pair 47 includes voltage-measuring electrodes 47A and 47B. The electrodes 47A and 47B are provided for the right half of the body. The voltage-measuring electrode pair 48 includes voltage-measuring electrodes 48A and 48B. The voltage-measuring electrodes 48A and 48B are provided for the left half of the body.

A line connecting the current-applying electrode 37A with the current-applying electrode 37B is defined as "inter-electrode line A7". A line connecting the current-applying electrode 38A with the current-applying electrode 38B is defined as "inter-electrode line A8". A line which passes through the current-applying electrode 37A and is in parallel to the body trunk axis CB is defined as a reference line LF. A line which passes through the current-applying electrode 37B and is in parallel to the body trunk axis CB is defined as a reference line LG. A line which passes through the current-applying electrode 38A and is in parallel to the body trunk axis CB is defined as a reference line LH. A line which passes through the current-applying electrode 38B and is in parallel to the body trunk axis CB is defined as a reference line LI.

Here, the body surface around the abdominal part 71 and the hip part 73 is cut along a line parallel to the body trunk axis CB in the center of the rear part 71B, and a development view in which this is developed into a plan view is assumed.

In the development view, the inter-electrode lines A7 and A8 are inclined with respect to the body trunk axis CB. In other words, the two electrodes included in each of the current-applying electrode pairs 37 and 38 are located at positions different from each other in the horizontal direction X and the vertical direction Y. The current-applying electrodes 37A and 37B are located at the same position in the vertical direction Y. The distance from the current-applying electrode 37A to the navel 72 is equal to the distance from the current-applying electrode 37B to the navel 72. The current-applying electrodes 38A and 38B are located at the same position in the vertical direction Y. The distance from the current-applying electrode 38A to the navel 72 is equal to the distance from the current-applying electrode 38B to the navel 72. Thus, the current-applying electrode pairs 37 and 38 are symmetrical with the navel 72 serving as the center.

When the range between the reference line LF and the reference line LG in the development view is defined as "inter-electrode range R4" and the range between the reference line LH and the reference line LI is defined as "inter-electrode range R5", the arrangement of the voltage-measuring electrode pairs 47 and 48 can be explained as below.

The voltage-measuring electrode pair 47 (electrodes 47A and 47B) is arranged in the inter-electrode range R4 in the development view. The electrodes 47A and 47B are arranged on the inter-electrode line A7. The middle position of the voltage-measuring electrode pair 47 coincides with the middle position of the current-applying electrode pair 37.

The voltage-measuring electrode pair 48 (48A and 48B) is arranged in the inter-electrode range R5 in the development view. The electrodes 48A and 48B are arranged on the inter-electrode line A8. The middle position of the voltage-measuring electrode pair 48 coincides with the middle position of the current-applying electrode pair 38.

When the measurement of the body fat 80 is started, the controlling unit 50 first supplies current between the current-applying electrode pair 37 and then supplies current between the current-applying electrode pair 38. Based on the voltage value measured by the voltage-measuring electrode pairs 47 and 48, the controlling unit 50 calculates the amount or volume of the body fat 80 between the electrodes 37A and 37B, between the electrodes 38A and 38B, and in the vicinity of the electrodes 37A, 37B, 38A, and 38B, and displays the calculation results on the display unit 23. Note that the measurement voltage of the voltage-measuring electrode pair 47 reflects the body fat 80 of the right half of the body while the measurement voltage of the voltage-measuring electrode pair 48 reflects the body fat 80 of the left half of the body. The controlling unit 50 may calculate the amount or volume of the body fat 80 in the right half and left half of the body and display the amount or volume of the body fat 80 in the right half and left half of the body in the display unit 23.

As thus described in detail, the present embodiment can provide the effects similar to the above (1) to (8), (10), and (11).

Seventh Embodiment

Figure 12:
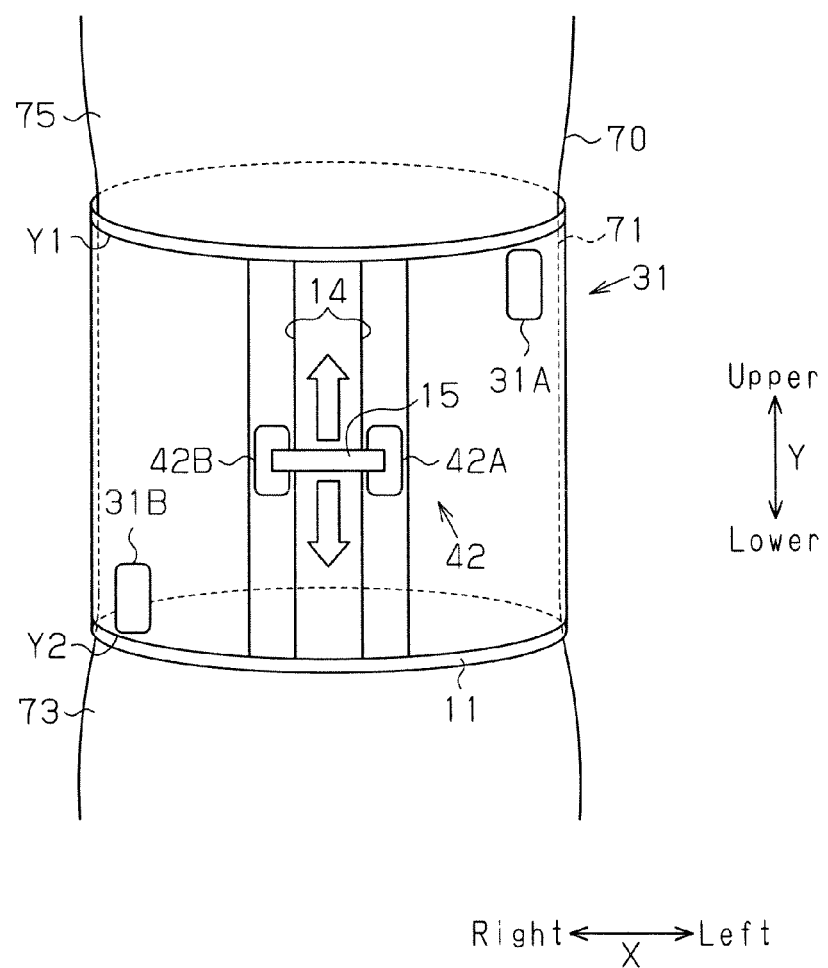
FIG. 12 is a schematic view indicating movable electrodes in a body fat measurement apparatus according to a seventh embodiment of the present invention.

With reference to FIG. 12, a point of the seventh embodiment of the present invention that is different from the second embodiment is described. The seventh embodiment is different from the second embodiment in the measuring part 20. The other points are similar to those in the second embodiment; therefore, the similar structures are denoted by the same reference symbols and description thereof is omitted.

As illustrated in FIG. 12, the voltage-measuring electrodes 42A and 42B are movable in the vertical direction Y. For example, the belt 11 can include a movable part 14 for moving the voltage-measuring electrodes 42A and 42B in the vertical direction Y. The movable part 14 includes a rail for sliding the voltage-measuring electrodes 42A and 42B. The voltage-measuring electrode 42A and the voltage-measuring electrode 42B are connected with each other via a connection part 15. When the connection part 15 is moved by a measurer, the electrodes 42A and 42B are moved integrally. The movable range of the electrodes 42A and 42B is from the upper end position to the lower end position of the movable part 14 in the vertical direction Y. While the voltage is measured, the electrodes 42A and 42B are fixed so as to be unmovable. The movable part 14 can have a structure, for example, for fixing the electrodes 42A and 42B at any position on the movable part 14.

As described above in detail, the present embodiment can provide the following effects in addition to effects similar to the above (1) to (8), and (14).

(16) The body fat measurement apparatus 10 includes the movable part 14 for moving the voltage-measuring electrodes 42A and 42B on the measured body 70; therefore, the voltage can be measured at various positions on the body surface without the provision of the plurality of voltage-measuring electrode pairs.

(17) The voltage-measuring electrode 42A and the voltage-measuring electrode 42B are connected with each other via the connection part 15. Therefore, the voltage can be measured at various positions on the body surface while the relative position between the voltage-measuring electrode 42A and the voltage-measuring electrode 42B is maintained constant.

Eighth Embodiment

Figure 13A:
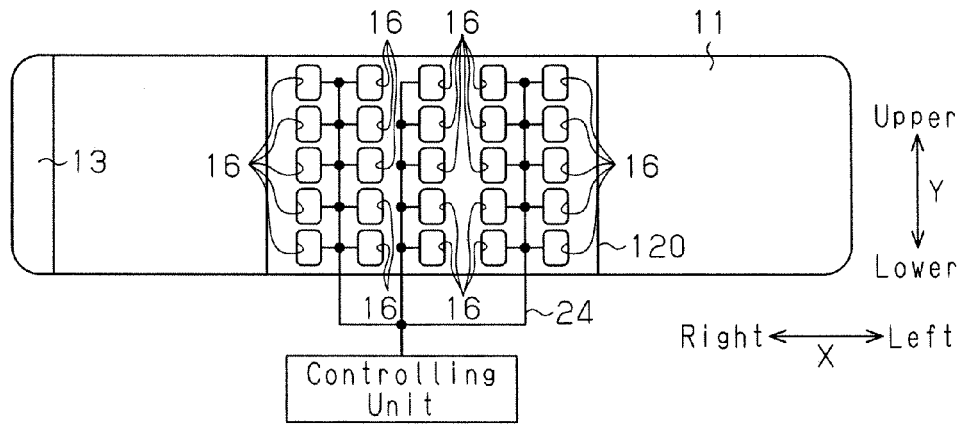
FIGS. 13A-13C each are a rear view of a body fat measurement apparatus according to an eighth embodiment of the present invention.
Figure 13B:
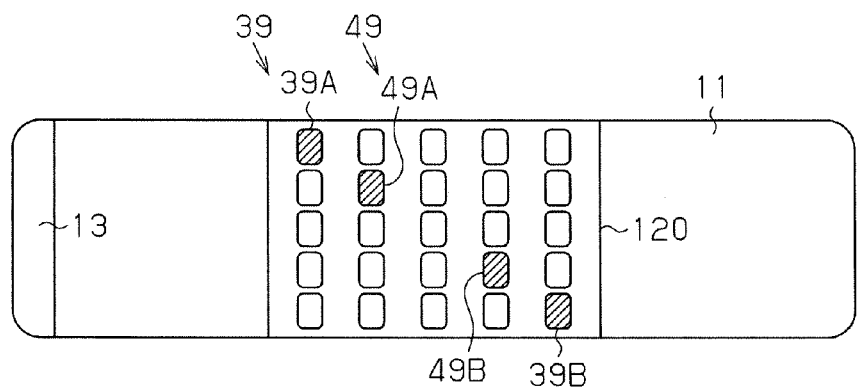
Figure 13C:
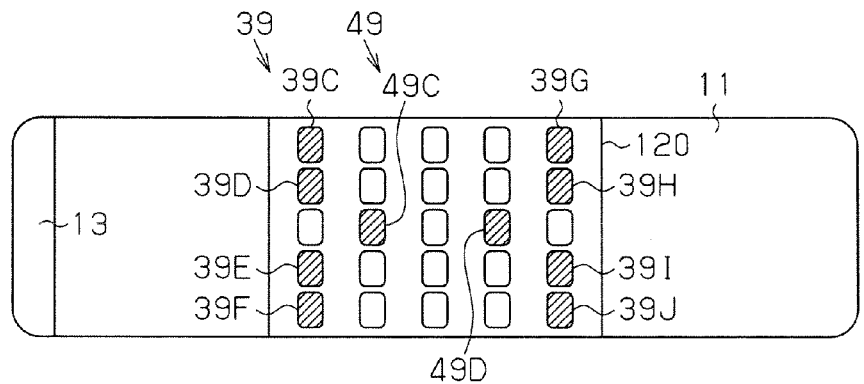

With reference to FIGS. 13A-13C, a point of the eighth embodiment of the present invention that is different from the first embodiment is described. The eighth embodiment is different from the first embodiment in the measuring part 20. The other points are similar to those in the first embodiment; therefore, the similar structures are denoted by the same reference symbols and description thereof is omitted.

As illustrated in FIG. 13A, a measuring part 120 of the body fat measurement apparatus 10 includes a plurality of disposing parts 16 for detachably attaching current-applying electrodes and voltage-measuring electrodes. In the illustrated example, twenty-five disposing parts 16 are provided in an array form of 5 rows×5 columns.

The transmission lines 24 connected to the controlling unit 50 are connected to the disposing parts 16. By fitting the current-applying electrodes or the voltage-measuring electrodes in the disposing parts 16, the current-applying electrodes or the voltage-measuring electrodes are electrically connected to the transmission lines 24. Some disposing examples of the current-applying electrodes or the voltage-measuring electrodes are described below.

In the example of FIG. 13B, a current-applying electrode 39A is attached to the disposing part 16 at a right upper end. A current-applying electrode 39B is attached to the disposing part 16 at a left lower end. A voltage-measuring electrode 49A is attached to the disposing part 16 which is below, and on the left side of the electrode 39A. A voltage-measuring electrode 49B is attached to the disposing part 16 which is above, and on the right side of the electrode 39B. The current-applying electrodes 39A and 39B constitute a current-applying electrode pair 39. The voltage-measuring electrodes 49A and 49B constitute a voltage-measuring electrode pair 49. The electrode arrangement of FIG. 13B corresponds to the electrode arrangement of the first embodiment (FIG. 2A).

In the example of FIG. 13C, four current-applying electrodes 39C, 39D, 39E, and 39F are attached to the disposing parts 16 in the right end column. Four current-applying electrodes 39G, 39H, 39I, and 39J are attached to the disposing parts 16 in the left end column. Voltage-measuring electrodes 49C and 49D are attached to the disposing part 16 more on the inside than the current-applying electrodes in the horizontal direction X and the vertical direction Y. The middle position of the voltage-measuring electrodes 49C and 49D coincides with the middle position of the two electrodes of each current-applying electrode pair. The current-applying electrodes 39C to 39J constitute the four current-applying electrode pairs 39. The voltage-measuring electrodes 49C and 49D constitute the voltage-measuring electrode pair 49. The electrode arrangement of FIG. 13C corresponds to the electrode arrangement of the fourth embodiment (FIG. 9).

As described so far, the present embodiment can provide the following effects in addition to the effects similar to the above (1) to (15).

(18) The body fat measurement apparatus 10 includes the disposing parts 16 for detachably attaching the current-applying electrodes and the voltage-measuring electrodes. The belt 11 supports the current-applying electrodes and the voltage-measuring electrodes attached to the disposing parts 16. Since the number and arrangement of the electrodes can be selected, the degree of freedom of measurement for the body fat can be increased.

The embodiments above can be modified as below, for example. The modified examples can be combined with each other.

Figure 14:
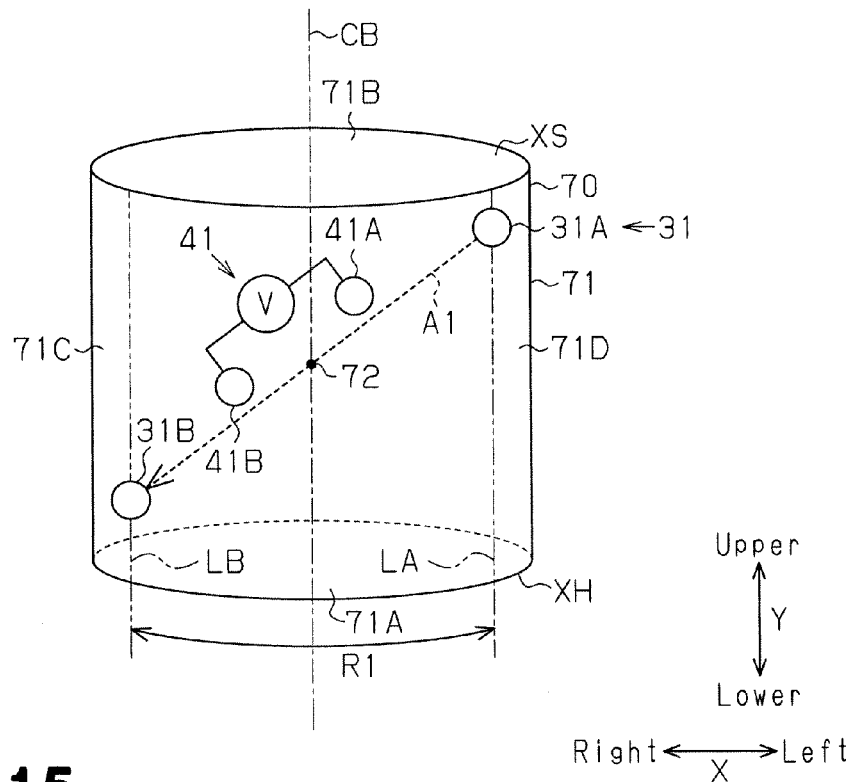
FIG. 14 is a schematic view indicating the positions of electrodes in a modified example.

Although the first embodiment provides the voltage-measuring electrode pair 41 on the inter-electrode line A1, the electrode pair 41 may be alternatively provided above the inter-electrode line A1 as illustrated in FIG. 14. Further alternatively, the voltage-measuring electrode pair can be provided below the inter-electrode line A1.

Although the adjacent electrodes 31A, 41A, 41B, and 31B are arranged at equal intervals in the first embodiment, the intervals may be various. The intervals may be changed as below.

The interval between the electrodes 31A and 31B is made smaller than that in the first embodiment.

The interval between the electrodes 31A and 31B is made larger than that in the first embodiment.

The interval between the electrodes 41A and 41B is made smaller than that in the first embodiment.

The interval between the electrodes 41A and 41B is made larger than that in the first embodiment.

Figure 15:
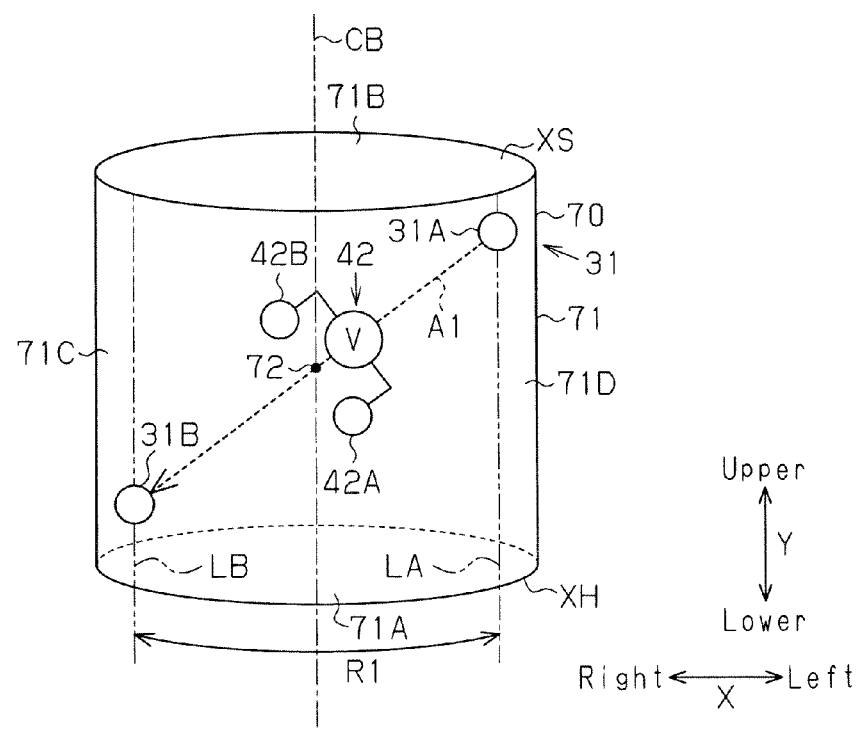
FIG. 15 is a schematic view indicating the positions of electrodes in another modified example.

Although the second embodiment provides the voltage-measuring electrodes 42A and 42B so that the positions of the electrodes 42A and 42B are the same in the vertical direction Y, the voltage-measuring electrode pair 42 can be arranged so that a line connecting the electrodes 42A and 42B with each other is inclined with respect to the body trunk axis CB, as illustrated in FIG. 15, for example. Alternatively, the voltage-measuring electrode pair 42 can be arranged so that the line connecting the electrodes 42A and 42B with each other is parallel to the body trunk axis CB.

In the third embodiment, the voltage-measuring electrode pair 43 and electrode pair 44 measure the body fat 80 in the right half and left half of the body, respectively. However, based on the measurement results on the half body by one electrode pair, the body fat of the other half of the body can be estimated. Alternatively, based on the measurement results on the half body, the entire body fat amount can be estimated.

In the third embodiment, current is fed in the order of the current-applying electrode pair 32 and the current-applying electrode pair 33 for measuring the body fat 80; however, the current can be fed to the electrode pairs 32 and 33 at the same time.

In the third embodiment, the current is fed from the shared current-applying electrode 32A to the current-applying electrodes 32B and 33B; however, the current may be fed from the current-applying electrodes 32B and 33B toward the current-applying electrode 32A.

In the fourth embodiment, the two electrodes of each of the current-applying electrode pairs 31, 34, 35, and 36 are arranged on the reference lines LA and LB, respectively.

However, the two electrodes of at least one electrode pair can be arranged on a different place from the reference lines LA and LB.

In the fourth embodiment, the electrodes are arranged so that the inter-electrode ranges R1 of the current-applying electrode pairs 31, 34, 35, and 36 have the same size; however, the electrodes may be arranged so that the inter-electrode ranges of the electrode pairs have different sizes from each other.

In the fourth embodiment, the four current-applying electrode pairs 31, 34, 35, and 36 are provided. However, the number of electrode pairs may be five or more. Alternatively, one, two, or three out of the four electrode pairs 31, 34, 35, and 36 may be omitted.

In the fifth embodiment, the voltage-measuring electrode pairs 42, 45, and 46 are arranged at equal intervals along the body trunk axis CB. However, for example, the interval between the electrode pair 42 and the electrode pair 45 may be different from the interval between the electrode pair 42 and the electrode pair 46. Alternatively, at least one middle position is not necessary to coincide with the body trunk axis CB.

In the fifth embodiment, the number of voltage-measuring electrode pairs 42, 45, and 46 may be four or more. Alternatively, one or two electrode pairs out of the three electrode pairs 42, 45, and 46 may be omitted.

In the seventh embodiment, the voltage-measuring electrodes 42A and 42B may be individually movable.

In the seventh embodiment, the electrodes 42A and 42B are fixed so as to be unmovable in measuring voltage; however, the voltage can be measured while the electrodes 42A and 42B are moved on the measured body 70 along a rail.

In the eighth embodiment, the number and arrangement of the disposing parts 16 can be changed as appropriate.

In the ninth embodiment, each disposing part 16 may be, for example, a hook that can be engaged with the measuring part 120 and the electrode.

In the first, second, and fifth embodiments, the current-applying electrode 31A is arranged on the left half of the body and the current-applying electrode 31B is arranged on the right half of the body; however, the electrode 31A may be arranged on the right half of the body and the electrode 31B may be arranged on the left half of the body while the positions thereof in the vertical direction Y are maintained as those in the above embodiments.

In the first, second, and fifth embodiments, the current-applying electrode 31A is arranged above the current-applying electrode 31B in the vertical direction Y; however, the electrode 31A can be arranged below the electrode 31B while the positions thereof in the horizontal direction X are maintained as those in the above embodiments.

In the above embodiments, the electrode pairs are arranged so that the middle positions of the current-applying electrode pair and the voltage-measuring electrode pair coincide with each other; however, the electrode pairs may be arranged so that the middle positions of the current-applying electrode pair and the voltage-measuring electrode pair are different from each other.

In the above embodiments, the body fat measurement apparatus 10 includes the belt 11 supporting the electrode. However, the belt 11 may be omitted. Alternatively, a bar-like or plate-like handle or knob that can be held by a measurer may be attached to the measuring part 20 instead of the belt 11. In this case, the measuring part 20 itself functions as the support member that supports the electrode.

In the above embodiments, the mark 12 is aligned at the breastbone lower end part 76 and the hipbone part 74; however, the mark may be provided in accordance with the navel 72 or the backbone 77 so that the mark is aligned at the navel 72 or the backbone 77.

In the above embodiment, the mark 12 that allows direct positioning with respect to the breastbone lower end part 76 and the hipbone 74 is provided; however, a scale part protruding upward from the belt 11 may be provided, and the distance from the breastbone lower end part 76 to the upper end of the belt 11 may be adjusted using this scale part.

In the above embodiments, the volume of the visceral fat 82 is displayed in the three-dimensional image on the display unit 23 as the measurement results of the body fat 80; however, the measurement results of the body fat 80 can be displayed in numerical value. In an example of this case, the volume of the visceral fat 82 is displayed for every part of the measured body 70 like "right part of abdominal part: 50 cm$^3$, upper part of abdominal part: 30 cm$^3$".

In the above embodiments, the amount of body fat is calculated based on the measured voltage and this is displayed on the display unit 23; however, the measured voltage can be displayed directly on the display unit 23.

In the above embodiments, the measurement results of the body fat 80 are displayed on the display unit 23; however, the method of transmitting the measurement results to a measurer is not limited thereto. For example, the display unit 23 may be further provided with, or may be replaced by a speaker that transmits the measurement results to the measurer via voice.

In the above embodiments, a conductive gel material may be used as the electrode material.

In the above embodiments, the operating unit 22, the display unit 23, and the controlling unit 50 may be provided for other members than the belt 11.

In the above embodiments, the power supply can be incorporated into the measuring part 20; however, the body fat measurement apparatus 10 may be provided with a power supply terminal for receiving power from an external power supply.

The posture of the measured body 70 when the body fat 80 is measured is not particularly limited; for example, the measured body 70 may stand up, sit down, or be supine.

The body fat measurement apparatus 10 in the above embodiments is optimized for the measurement of the body fat 80 in the range from the breastbone plane XS to the hipbone plane XH but can be modified so as to measure the body fat in another part of the body trunk (for example, breast part or hip), or in a limb such as an arm or a leg. For example, the size and shape of each part of the body fat measurement apparatus 10 can be changed in accordance with the other part of the body trunk or the limb. For measuring the body fat in the limb, a longitudinal axis of the limb may be used instead of the body trunk axis CB as one reference of the measurement position. The body trunk axis and the limb axis are examples of the body axis.

In the above embodiments, a human body is described as an example of the measured body 70; however, the measured body 70 may be an animal instead of the human body.

DESCRIPTION OF THE REFERENCE CHARACTERS

10: body fat measurement apparatus; 11: belt; 11A: rear surface; 11B: front surface; 12, 12A, 12B: marks; 13: fastener; 14: movable part; 15: connection part; 16: disposing part; 20, 120: measuring part; 21: detection plane; 22: operating unit; 23: display unit; 24: transmission line; 31 to 39: current-applying electrode pair; 31A, 31B, 32A, 32B, 33B, 34A, 34B, 35A, 35B, 36A, 36B, 37A, 37B, 38A, 38B, 39A to 39J: current-applying electrode; 41 to 49: voltage-measuring electrode pair; 41A, 41B, 42A, 42B, 43A, 43B, 44A, 44B, 45A, 45B, 46A, 46B, 47A, 47B, 48A, 48B, 49A TO 49D: voltage-measuring electrode; 50: controlling unit (computing circuit); 70: measured body; 71: abdominal part; 71A: front part; 71B: rear part; 71C: right flank; 71D: left flank; 72: navel; 73: hip part; 74: hipbone part; 75: breast part; 76: breastbone lower end part; 77: backbone; 80: body fat; 81: subcutaneous fat; 82: visceral fat; 83: muscle.

The invention claimed is:

1. A body fat measurement apparatus, comprising:
a flexible support member having a longitudinal axis;
a sole current-applying electrode pair of a first current-applying electrode and a second current-applying electrode;
a sole voltage-measuring electrode pair of a first voltage-measuring electrode and a second voltage-measuring electrode, wherein
the current-applying electrode pair and the voltage-measuring electrode pair are supported by the support member and aligned on a straight line inclined with respect to the longitudinal axis of the support member, and the voltage-measuring electrode pair is arranged between the first current-applying electrode and the second current-applying electrode; and
a controlling unit that calculates the amount of body fat based solely on a measured voltage value measured by the voltage-measuring electrode pair supported by the support member and aligned on the inclined straight line when current is applied via the first and second current-applying electrodes of the current-applying electrode pair supported by the support member and aligned on the inclined straight line.

2. The body fat measurement apparatus according to claim 1, wherein the support member includes a belt having a shape configured to be wound around a body to be measured to fix the current-applying electrode pair and the voltage-measuring electrode pair to the body to be measured.

3. The body fat measurement apparatus according to claim 1, wherein the support member includes disposing parts on which the current-applying electrode and the voltage-measuring electrode are detachably attached.

4. The body fat measurement apparatus according to claim 1, further comprising a mark formed on the support member and configured to indicate a reference position corresponding to a navel, a hipbone, or a backbone of the body to be measured to set the positions of the current-applying electrode pair and the voltage-measuring electrode pair.

5. The body fat measurement apparatus according to claim 1, wherein the controlling unit includes a computing circuit configured to calculate a volume of body fat based on a voltage measured by the voltage-measuring electrode pair.

6. The body fat measurement apparatus according to claim 1, comprising a display unit configured to display three-dimensional distribution of body fat based on the voltage measured by the voltage-measuring electrode pair.

7. A body fat measurement apparatus that measures a body fat by measuring voltage of a body to be measured when current is applied to the body to be measured, the apparatus comprising:
a sole current-applying electrode pair of a first current-applying electrode and a second current-applying electrode;
a sole voltage-measuring electrode pair of a first voltage-measuring electrode and a second voltage-measuring electrode;
an elongated, flexible support member having a longitudinal axis, wherein
the current-applying electrode pair and the voltage-measuring electrode pair are supported by the support member and aligned on a straight line inclined with respect to the longitudinal axis of the support member, and the voltage-measuring electrode pair is supported by the support member between the first current-applying electrode and the second current-applying electrode; and
a controlling unit that calculates the amount of body fat based solely on a measured voltage value measured by the voltage-measuring electrode pair supported by the support member and aligned on the inclined straight line when current is applied via the first and second current-applying electrodes of the current-applying electrode pair supported by the support member and aligned on the inclined straight line.

8. The body fat measurement apparatus according to claim 7, wherein the first current-applying electrode, the second current-applying electrode, the first voltage-measuring electrode, and the second voltage-measuring electrode are aligned on a common straight line inclined with respect to the longitudinal axis of the support member.

9. The body fat measurement apparatus according to claim 7, wherein:
when the support member is wound around the body to be measured, the support member is fixed to the body to be measured by the support member, and the current-applying electrode pair supported by the support member is placed at a position determined so that a line connecting the first current-applying electrode with the second current-applying electrode is inclined with respect to a body axis of the body to be measured.

10. A manufacturing method for the body fat measurement apparatus according to claim 7, the method comprising:
supporting the current-applying electrode pair and the voltage-measuring electrode pair by the support member, wherein the current-applying electrode pair and the voltage-measuring electrode pair are aligned on a straight line inclined with respect to the longitudinal axis of the support member, and the voltage-measuring electrode pair is arranged between the first current-applying electrode and the second current-applying electrode; and
connecting the controlling unit with the current-applying electrode pair and the voltage-measuring electrode pair.

* * * * *